(12) United States Patent  
Salter

(10) Patent No.: US 8,989,478 B2
(45) Date of Patent: Mar. 24, 2015

(54) METHOD AND SYSTEM FOR VISUALIZATION OF SEMICONDUCTOR WAFER INSPECTION DATA ACQUIRED IN A PHOTOVOLTAIC CELL PRODUCTION PROCESS

(75) Inventor: Robert J. Salter, Saint Albans, VT (US)

(73) Assignee: KLA-Tencor Corporation, Milpitas, CA (US)

( * ) Notice: Subject to any disclaimer, the term of this patent is extended or adjusted under 35 U.S.C. 154(b) by 314 days.

(21) Appl. No.: 13/559,175

(22) Filed: Jul. 26, 2012

(65) Prior Publication Data

US 2013/0028506 A1   Jan. 31, 2013

Related U.S. Application Data

(60) Provisional application No. 61/513,212, filed on Jul. 29, 2011.

(51) Int. Cl.
*G06K 9/00* (2006.01)
*G01N 21/88* (2006.01)
*G01N 21/95* (2006.01)

(52) U.S. Cl.
CPC ........ *G01N 21/8851* (2013.01); *G01N 21/9501* (2013.01)
USPC ...................................................... 382/145

(58) Field of Classification Search
None
See application file for complete search history.

(56) References Cited

U.S. PATENT DOCUMENTS

| | | | |
|---|---|---|---|
| 4,951,190 A | 8/1990 | Lane et al. | |
| 5,226,118 A | 7/1993 | Baker et al. | |
| 5,841,893 A * | 11/1998 | Ishikawa et al. | 382/145 |
| 6,542,830 B1 | 4/2003 | Mizuno et al. | |
| 6,611,728 B1 * | 8/2003 | Morioka et al. | 700/109 |
| 6,744,266 B2 * | 6/2004 | Dor et al. | 324/754.22 |
| 7,343,583 B2 * | 3/2008 | Keck et al. | 716/51 |
| 7,474,986 B2 | 1/2009 | Teshima et al. | |
| 7,570,797 B1 | 8/2009 | Wang et al. | |
| 2001/0051836 A1 | 12/2001 | Lamey, Jr. et al. | |
| 2004/0168115 A1 | 8/2004 | Bauernschmidt et al. | |
| 2006/0009943 A1 | 1/2006 | Keck et al. | |
| 2010/0211903 A1 | 8/2010 | Luque | |

FOREIGN PATENT DOCUMENTS

WO    WO2006/017154    2/2006

* cited by examiner

*Primary Examiner* — Daniel Mariam
(74) *Attorney, Agent, or Firm* — Suiter Swantz pc llo

(57) ABSTRACT

A system for providing visualization of semiconductor wafer inspection data acquired during in a photovoltaic cell production process includes a display device, a user interface device, and a computer control system configured for: receiving one or more inspection data sets acquired from each of a plurality of semiconductor wafers using a plurality of wafer process tools of a photovoltaic cell production line; generating an aggregated hierarchical wafer data gallery utilizing the received one or more inspection data sets; and displaying at least a portion of the aggregated hierarchical wafer data gallery in the gallery display area of the display device.

22 Claims, 8 Drawing Sheets

| Product | Process | Ingot | Cassette | Wafer | Defects | Tool Type | Tool Id | TimeOfDay | Operator |
|---|---|---|---|---|---|---|---|---|---|
| ⊞ Product | Process | Ingot | 29097 | Wafer 7 | | PVI | PVI-1 | 51956 | Operator |
| ⊟ Product | Process | Ingot | 29098 | Wafer 8 | | PVI | PVI-1 | 51958 | Operator |
| Defect Id | Type | Sub Type | | X Loc | Y Loc | Width | Hight | Angle | |
| 1 | Surface | Small bright defect | | 78.159 | -52.011 | 2.273 | 0.062 | 0.000 | |
| 2 | Surface | Small bright defect | | 46.336 | 37.758 | 0.797 | 0.206 | 0.000 | |
| 3 | Surface | Small bright defect | | 78.077 | 58.719 | 25.397 | 0.189 | 0.000 | |
| 4 | Surface | Small bright defect | | -0.015 | -63.140 | 156.857 | 32.868 | 0.000 | |
| 5 | Surface | Small bright defect | | -0.651 | 66.696 | 157.436 | 32.484 | 0.000 | |
| 6 | Surface | Scratch | | 78.077 | 58.719 | 25.379 | 0.189 | 0.000 | |
| 7 | Surface | Scratch | | 78.159 | -52.011 | 2.237 | 0.062 | 0.000 | |
| 8 | Surface | Scratch | | -78.068 | 13.094 | 0.737 | 0.061 | 0.000 | |
| ⊞ Product | Process | Ingot | 29099 | Wafer 13 | | PVI | PVI-1 | 51962 | Operator |
| ⊞ Product | Process | Ingot | 29100 | Wafer 9 | | PVI | PVI-1 | 51964 | Operator |
| ⊞ Product | Process | Ingot | 29101 | Wafer 6 | | PVI | PVI-1 | 51968 | Operator |
| ⊞ Product | Process | Ingot | 29102 | Wafer 24 | | PVI | PVI-1 | 51970 | Operator |
| ⊞ Product | Process | Ingot | 29103 | Wafer 28 | | PVI | PVI-1 | 51972 | Operator |
| ⊞ Product | Process | Ingot | 29104 | Wafer 4 | | PVI | PVI-1 | 51976 | Operator |
| ⊞ Product | Process | Ingot | 29105 | Wafer 8 | | PVI | PVI-1 | 51980 | Operator |
| ⊞ Product | Process | Ingot | 29106 | Wafer 10 | | PVI | PVI-1 | 51982 | Operator |

FIG.1C

METHOD AND SYSTEM FOR VISUALIZATION OF SEMICONDUCTOR WAFER INSPECTION DATA ACQUIRED IN A PHOTOVOLTAIC CELL PRODUCTION PROCESS

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a regular (non-provisional) patent application of United States Provisional Patent Application entitled METHOD AND SOFTWARE PRODUCT FOR INSPECTION OF WAFERS DURING THE PRODUCTION PROCESS FOR SOLAR CELLS, naming Robert J. Salter, as an inventor, filed Jul. 29, 2011 Application Ser. No. 61/513,212.

TECHNICAL FIELD

The present invention generally relates to the visualization of semiconductor wafer data and, in particular, to the visualization of inspection data acquired from a semiconductor wafer during a photovoltaic device production process.

BACKGROUND

As the demand for semiconductor devices increases the need for improved handling of semiconductor characterization data also increases. Wafer inspection data is commonly acquired via optical inspection tools from one or more wafer processing tools of semiconductor device fabrication lines. This acquired inspection data may be used to track the quality of fabricated semiconductor devices at each step of the semiconductor device production process, allowing a user to reject sub-standard devices and/or adjust the fabrication process in order to bring subsequently process devices within a selected tolerance level. The analysis of the wafer inspection data involves handling large volumes of both text- and image-based data associated with the various wafers being processed in the production line. In the case of photovoltaic device fabrication, particularly solar cell fabrication, the volume of wafer processing is generally very large even when compared to other semiconductor processing settings. As a result, the need for improved textual and imagery data handing is heightened. As such, it would be advantageous to provide a system and method that provides a more efficient and flexible data handling capabilities.

SUMMARY

A system for providing visualization of semiconductor wafer inspection data acquired in a photovoltaic cell production process is disclosed. In one aspect, the system may include, but is not limited to, a display device, wherein the display device includes at least a data gallery display area and an imagery display area; a user interface device; a computer control system communicatively coupled to the display device and the user interface device, the computer control system configured for: receiving one or more inspection data sets acquired from each of a plurality of semiconductor wafers using a plurality of inspection devices associated with a plurality of wafer process tools of a photovoltaic cell production line; generating an aggregated hierarchical wafer data gallery utilizing the received one or more inspection data sets; and displaying at least a portion of the aggregated hierarchical wafer data gallery in the gallery display area of the display device.

A method for providing visualization of semiconductor wafer inspection data acquired in a photovoltaic cell production process is disclosed. In one aspect, the method may include, but is not limited to, providing a display device including at least a gallery display area and an image display area, the display device being responsive to one or more user interface devices; receiving one or more inspection data sets acquired from each of a plurality of semiconductor wafers using a plurality of inspection devices associated with a plurality of wafer process tools of a photovoltaic cell production line; generating an aggregated hierarchical wafer data gallery utilizing the received one or more inspection data sets; displaying a plurality of wafer data sets of the aggregated hierarchical wafer data gallery in the gallery display area of the display device; and responsive to a signal from the user interface device indicative of a selection of a wafer for defect data display, hierarchically displaying one or more sets of wafer defect data associated with the wafer in the gallery display area of the display device.

A method for providing visualization of semiconductor wafer inspection data acquired in a photovoltaic cell production process is disclosed. In one aspect, the method may include, but is not limited to, providing a display device including at least a gallery display area and an image display area, the display device being responsive to one or more user interface devices; one or more inspection data sets acquired from each of a plurality of semiconductor wafers using a plurality of inspection devices associated with a plurality of wafer process tools of a photovoltaic cell production line; generating an aggregated hierarchical wafer data gallery utilizing the received one or more inspection data sets; displaying a plurality of wafer group data sets of the aggregated hierarchical wafer data gallery in the gallery display area of the display device; responsive to a signal from the user interface device indicative of a selection of a wafer group for wafer display, hierarchically displaying one or more sets of wafer data associated with each wafer of the wafer group in the gallery display area of the display device; and responsive to a signal from the user interface device indicative of a selection of a wafer of the wafer group for defect data display, hierarchically displaying one or more sets of wafer defect data associated with the wafer in the gallery display area of the display device.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which:

FIG. 1C is a schematic diagram of an enlarged view of a gallery display area of a display, in accordance with one embodiment of the present invention.

DETAILED DESCRIPTION OF THE INVENTION

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention. Reference will now be made in detail to the subject matter disclosed, which is illustrated in the accompanying drawings.

Referring generally to FIG. 1A through 1F, a system 100 for providing visualization of semiconductor wafer inspection data acquired in a photovoltaic cell production process is described in accordance with the present disclosure. The present invention is directed to a system and method for dynamically and efficiently grouping, arranging and visualizing textual- and image-based wafer data during a photovoltaic cell production process. The present invention allows a user to automatically collect wafer inspection data from multiple process tools of a photovoltaic device fabrication line, avoiding the need to manually acquire the inspection data from each individual process tool. The automatically acquired inspection data is then displayed in an aggregated hierarchical gallery, known as a "tree" gallery, providing the user with efficient visualization and manipulation of the various wafer inspection data sets acquired from the various tools of the photovoltaic cell process line. Due to the significant amount of inspection data acquired during typical photovoltaic cell fabrication process, the present invention provides significant benefits to a user.

Figure 1A:
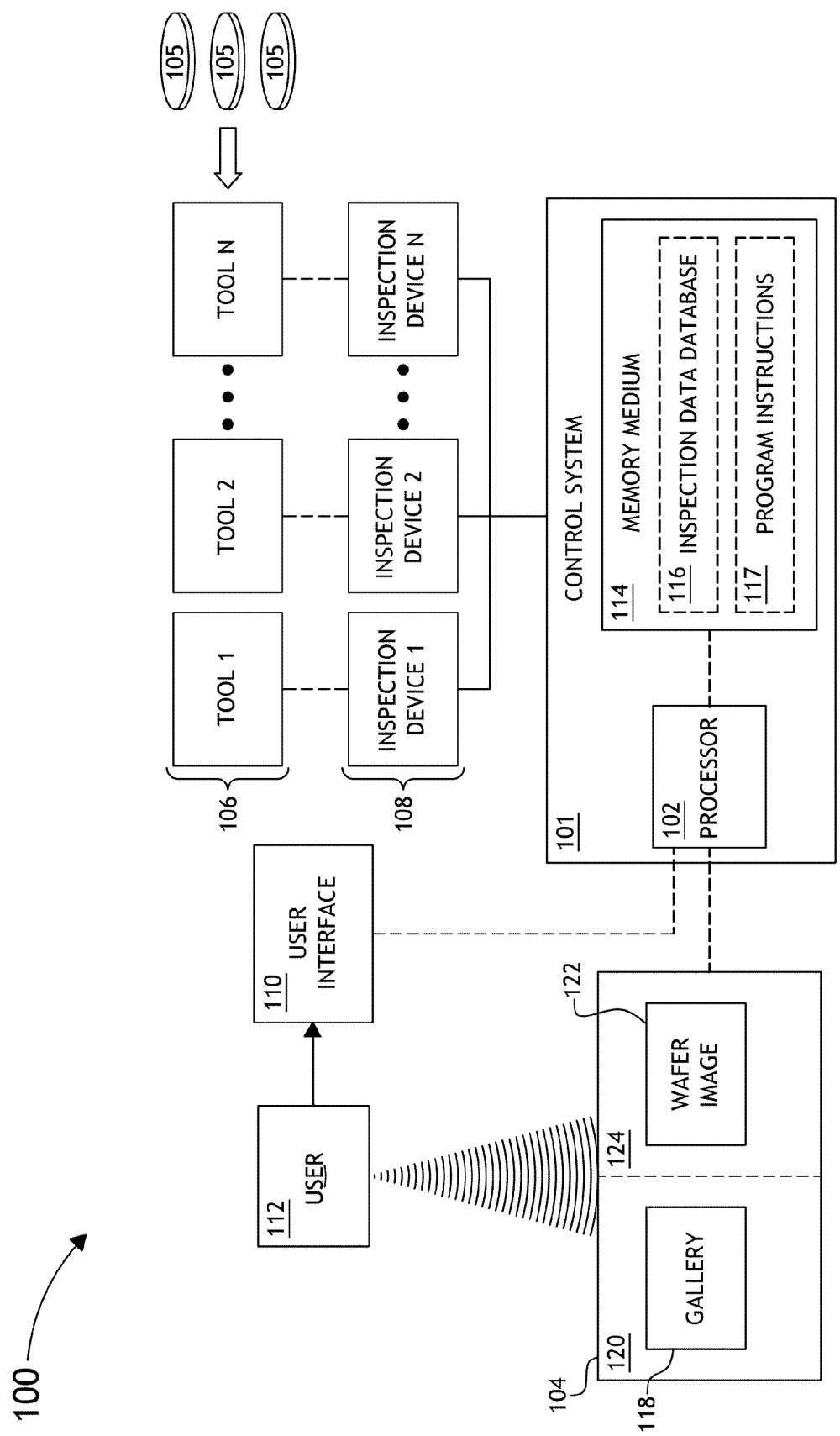
FIG. 1A is a block diagram view of a system for providing visualization of semiconductor wafer inspection data acquired in a photovoltaic cell production process, in accordance with one embodiment of the present invention.

FIG. 1A illustrates a block diagram view of the system 100 for providing visualization of semiconductor wafer characterization data, in accordance with one embodiment of the present invention. The system 100 may include a computer control system 101 equipped with one or more processors 102, and a display device 104 and a user interface device 110 communicatively coupled to the one or more processors 102 of the control system 101. The computer control system 101 may further include a non-transitory storage medium 114 (i.e., memory medium) containing program instructions configured to cause the one or more processors 102 to carry out the various steps described through the present disclosure.

In one aspect of the present invention, the one or more processors 102 of the control system 100 are configured to: receive one or more inspection data sets acquired from each of a plurality of semiconductor wafers 105 using a plurality of inspection devices 108 associated with a plurality of wafer process tools 106 of a photovoltaic cell production line (i.e., process suitable for creating photovoltaic cells utilizing the plurality of semiconductor wafers 105); generate an aggregated hierarchical wafer data gallery 118 utilizing the received one or more inspection data sets; and display at least a portion of the aggregated hierarchical wafer data gallery 118 in the gallery display area 120 of the display device 104.

In one embodiment of the present invention, the one or more processors 102 of the controller 102 may receive inspection data of a plurality of semiconductor wafers 105 from a plurality of inspection devices 108 (e.g., inspection device 1, inspection device 2, and up to and including inspection device N) associated with a plurality of wafer process tools 106 (e.g., process tool 1, process tool 2, and up to and including process tool N). In this regard, each process tool of the plurality of tools 106 may be associated with an inspection device, such as inspection device 1, inspection device 2, and inspection device N, which are configured to acquire imagery data of the surface of the semiconductor wafers 105 as they are processed by the respective process tools 106 utilizing an optical detector (e.g., CCD camera). In one embodiment, each process tool may be equipped with an integrated inspection system. In another embodiment, each process tool may be associated with a standalone inspection system. In a further embodiment, each of the plurality of inspection systems 108 may be communicatively coupled to the control system 101 via a data coupling (e.g., wireline data coupling or wireless data coupling). For example, each of the plurality of inspection system 108 may transmit inspection data to the one or more processors of the control system 101 via a data connection. In another example, each of the plurality of inspection system 108 may transmit inspection data to an inspection data database 116 of the memory 114 of the control system 101 via a data connection. In this regard, the inspection data may be maintained in the memory 114 and retrieved at a later time by processor 102, allowing the system 100 to perform the various steps of the present invention at any time following inspection of the wafers 105.

FIGS. 1B through 1F illustrate various schematic view of the gallery display area 120 and the image display area 124 of display device 104. In one aspect, in generating and displaying an aggregated hierarchical wafer data gallery 118, the one or more processors 102 the control system 101 may define a plurality of data grouping levels of the received one or more inspection data sets acquired from each of a plurality of semiconductor wafers. In this sense, a user 112 (via the user interface device 110 and one or more processors 102) may dynamically group and organize data retrieved from the various inspection devices 108 associated with the process tools 106 in a selected hierarchical manner. For example, a user 112 may transmit a retrieval command to the one or more processors 102 of the control system 101. The one or more processors 102 may then retrieve the inspect data associated with each of the wafers 105 during the various steps of the photovoltaic cell fabrication process. In response to a user selection of the data grouping configuration, the one or more processors 102 may then generate and display a gallery 118 according to the selected data grouping configuration selected by the user 112. Once the wafer data is loaded into gallery 118, the user may dynamically create a "tree view" of the various wafer data, define the different levels of wafer data grouping, and identify the type of statistics to include in the tree view of the wafer data.

Figure 1B:
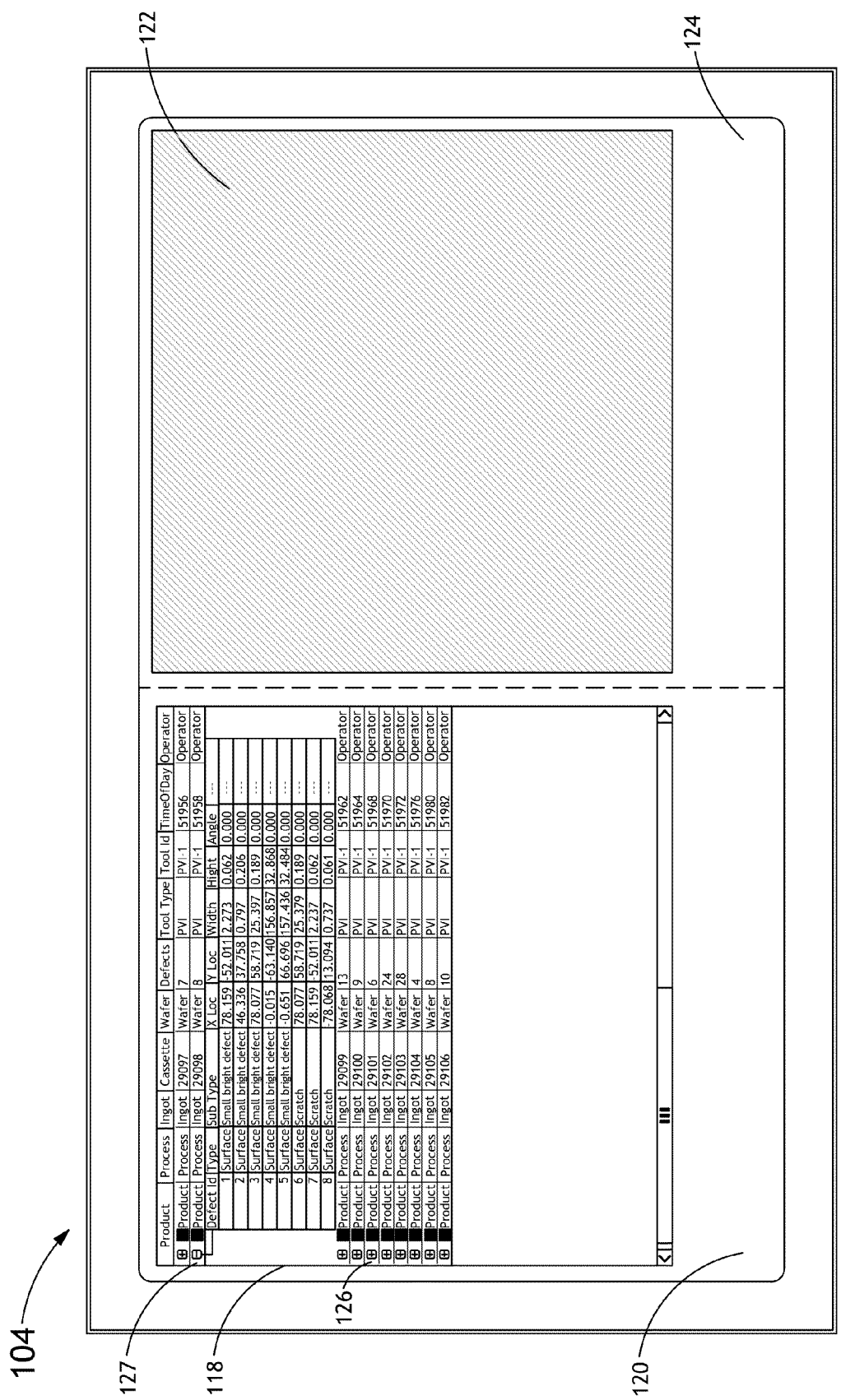
FIG. 1B is a schematic diagram of a display including a gallery display area and an image display area, in accordance with one embodiment of the present invention.

In one embodiment, as shown in FIGS. 1B and 1C, the one or more processors 102 may generate and display a dynamically responsive hierarchical gallery 118. In this regard, the one or more processors 102 may display a plurality of wafer data sets 126 of the aggregated hierarchical wafer data gallery 118 in the gallery display area 120 of the display device 104, in which each row 126 in the gallery 118 represents data associated with one wafer of a group of wafers. Utilizing the gallery 118 of FIGS. 1B and 1C, a user may select a given wafer row for auto-spawning of defect data 128 associated with the selected wafer. In response to a signal transmitted by the user interface device 110 indicative of a selection of a wafer row 126 for defect data display, the one or more processors 102 may hierarchically display one or more sets of wafer defect data associated with the wafer corresponding to the selected row in the gallery display area 120 of the display device 104. For example, as shown in FIG. 1C, the wafer of the second row of the gallery 118 includes eight defects. Selection of a wafer row 126 causes the defect data 128 associated with the plurality of defects of the wafer to be displayed in a series of defect data rows 130. This feature allows user to select a given wafer having a set of identified number of defects for further analysis. The defect data of each row 130 may include various defect parameters. For example, the defect data may include, but is not limited to, spatial position (e.g., X-Y position characterized by X Loc and Y Loc of FIG. 1C) of one or more defects of the wafer 105, size of one or more defects (e.g., characterized by Width, Height of FIG. 1C) of the wafer 105, angle of one or more defects (e.g., characterized by Angle of FIG. 1C), a description of the one or more defects (e.g., characterized by "type" and "sub type" of FIG. 1C), a defect identification number, and the like. It is noted herein that the specific layout of the set of defect data 128 is not limiting and should be interpreted merely as illustrative.

Figure 1D:
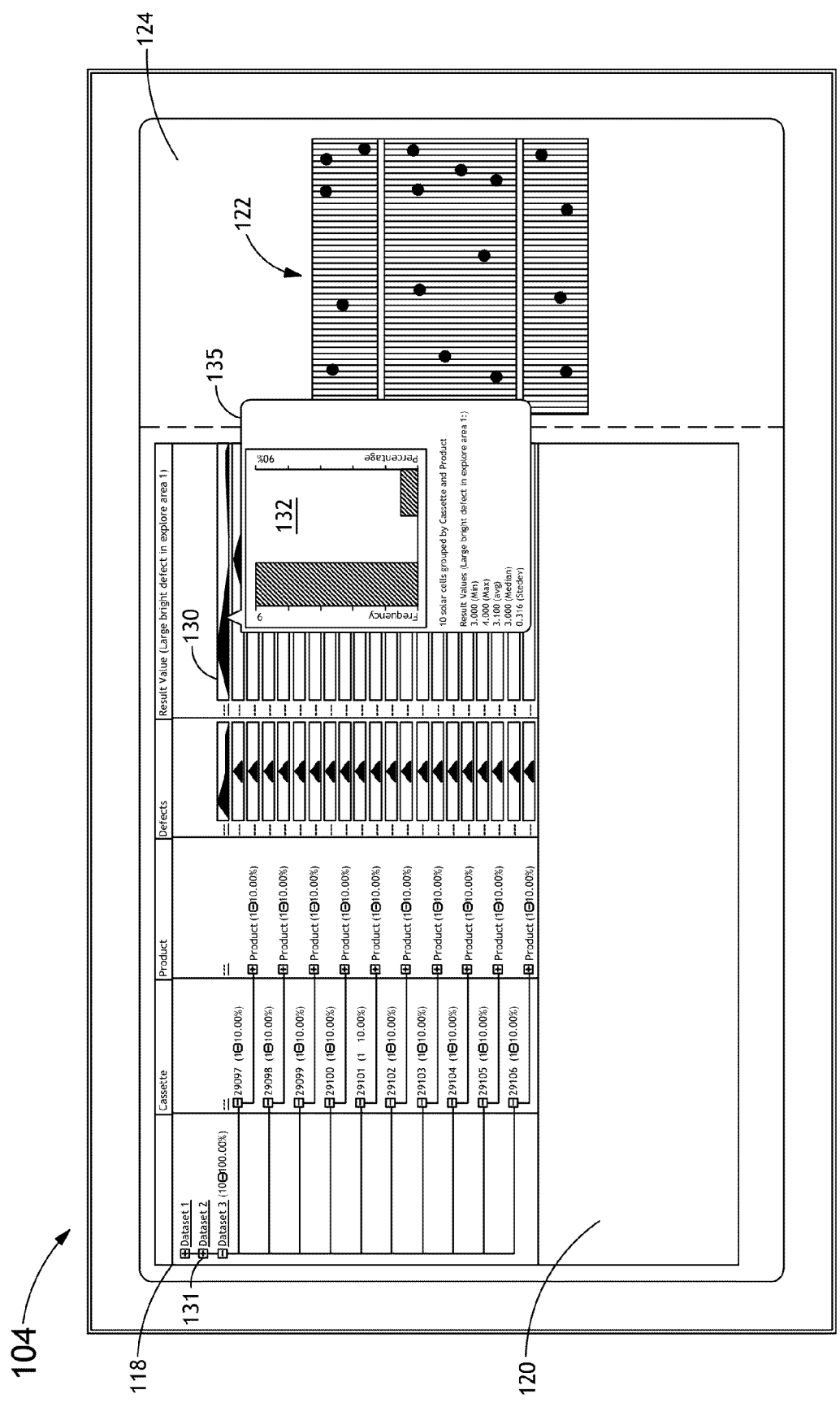
FIG. 1D is a schematic diagram of a display including a gallery display area and an image display area, in accordance with one embodiment of the present invention.
Figure 1E:
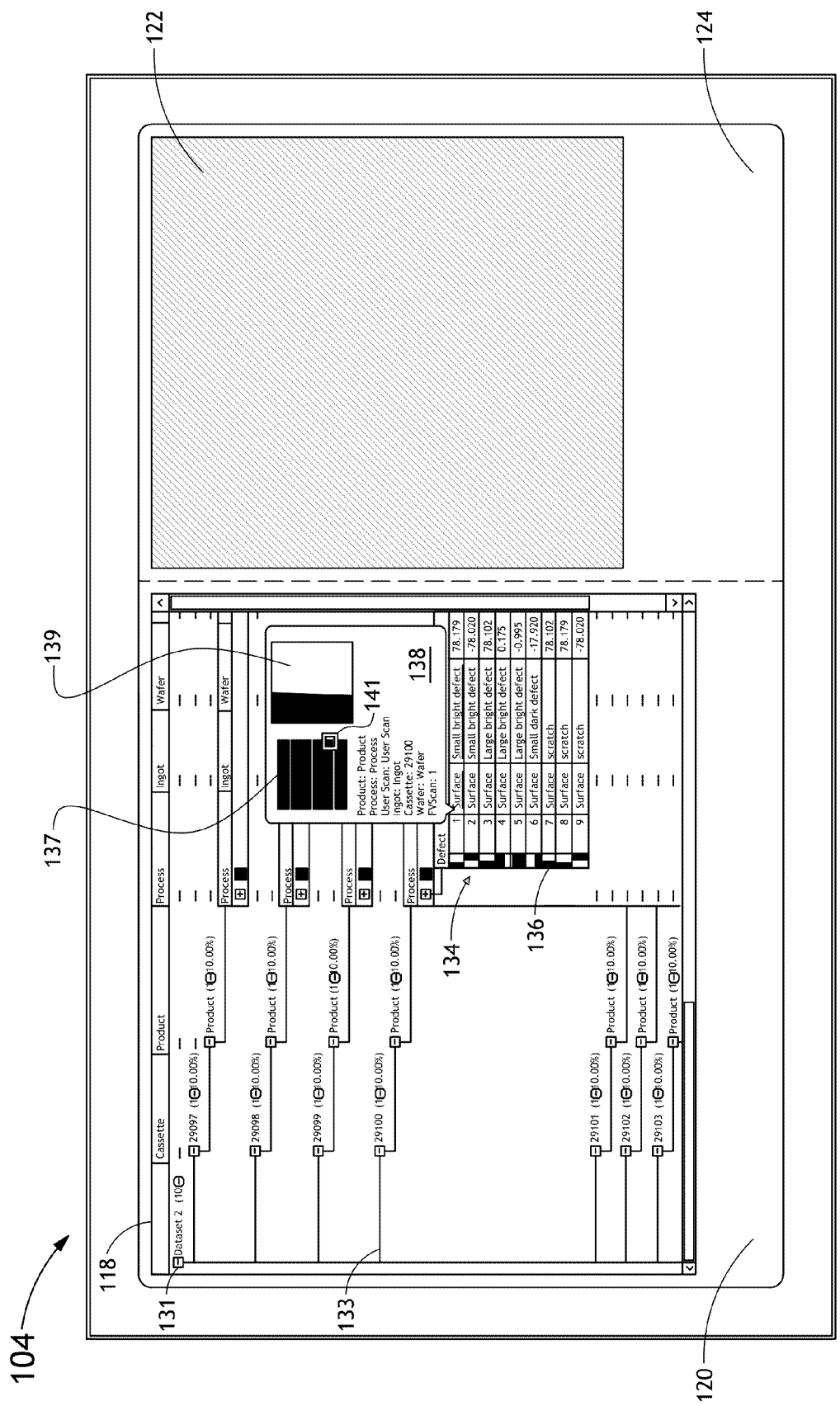
FIG. 1E is a schematic diagram of a display including a gallery display area and an image display area, in accordance with one embodiment of the present invention.

In an alternative embodiment, as shown in FIGS. 1D and 1E, the one or more processors 102 may generate and display a dynamically responsive hierarchical gallery 118 having an additional level of wafer grouping. In this regard, the one or more processors 102 may display a plurality of wafer group data sets 131 of the aggregated hierarchical wafer data gallery 118 in the gallery display area 120 of the display device 104, in which each row 131 in the gallery 118 represents data associated with one group of wafers of a plurality of a groups of wafers and associated with each individual wafer is defect data. Utilizing the gallery 118 of FIGS. 1D and 1E, a user may select a given wafer group row 131 for auto-spawning of wafer data 133 associated with each wafer in the wafer group of row 131. In turn, a user 112 may then select a given wafer row 133 of the wafer group 131 in order to auto-spawn defect data 134 associated with the selected wafer of row 133 of wafer group 131.

In response to a signal transmitted by the user interface device 110 indicative of a selection of a wafer group row 131 for individual wafer row 133 display, the one or more processors 102 may hierarchically display one or more sets of wafer data associated with the wafer group corresponding to the selected wafer group row in the gallery display area 120 of the display device 104. For example, as shown in FIG. 1D, the wafer group 131 of the third row of the gallery 118 includes ten wafers. Selection of a wafer group row 131 causes the wafer data associated with each of the group of wafers 131 to be displayed in a series of wafer data rows 133. The wafer data of each row 133 may include various wafer parameters (see FIG. 2 for listing of parameters). For example, the columns of the gallery 118 are related to the product "Product," the production process "Process" being carried out, the ingot "Ingot" from which the wafers are cut, the cassette number "cassette" in which the wafers to be processed are placed, the wafer number "Wafer," the number of defects "Defects" detected on the wafer 105, the process tool "Tool Type," the identification number of the process tool "Tool Id," the time of processing "TimeOfDay," and the name of the operator "Operator" using a specific process tool. It is noted herein that the specific layout of each wafer row 133 is not limiting and should be interpreted merely as illustrative.

In turn, in response to a signal transmitted by the user interface device 110 indicative of a selection of a wafer row 133 for defect data display, the one or more processors 102 may hierarchically display one or more sets of wafer defect data associated with the wafer 105 corresponding to the selected wafer row of the wafer group in the gallery display area 120 of the display device 104. For example, as shown in FIG. 1E, the wafer corresponding to the fourth wafer row 133 of the group of wafers 131 includes nine defects. Selection of a wafer row 133 causes the defect data 134 associated with the plurality of defects of the wafer 105 to be displayed in a series of defect data rows 136. As in FIGS. 1B and 1C, the defect data of each row may include various defect parameters (see FIGS. 1B and 1C for listing of defect parameters).

In the case of the grouped view of the gallery 118, the user 112 may dynamically change the grouping rules by simply dragging one or more of the columns of gallery 118 and moving them to the left or right. In this regard, the data is grouped from left to right. In addition, the user 112 may define and save to memory 114 grouping rules and then later apply the saved grouping rules to any group of wafer data that is displayed on the display device 104. Utilizing the user interface device 110 and the display device 104, the user 112 may select multiple groups or individual wafers 105 for more detailed analysis.

Referring again to FIG. 1D, the one or more processors 102 of the control system 101 may display a selected set of statistical characteristics associated with a selected portion of the received one or more inspection data sets acquired from each of a plurality of semiconductor wafers. In one embodiment, the one or more processors 102 of the control system 101 may display a summary 130 of statistical characteristics associated with a selected portion of the received one or more inspection data sets acquired from each of a plurality of semiconductor wafers. For example, the statistical summary 130 may provide a summary of a given statistical characteristic (e.g., frequency of size of defects) for the defects of a selected wafer.

In another embodiment, the one or more processors 102 of the control system 101 may display one or more statistical distribution charts, such as a histogram for a given data field, associated with a selected wafer group data set. In a further embodiment, in response to a signal from the user interface device 110 indicative of a selection of a selected wafer group data set, the one or more processors 102 may display one or more statistical distribution charts associated with a selected wafer group data.

The one or more processors 102 of the control system 101 are configured to allow for dynamic grouping of data fields and the ordering of the wafer and wafer group data as desired by a user 112. Each time wafer data is regrouped by a user via user interface 110 and processor 102, the processor 102 acts to recalculate the various statistical parameters as necessary. For example, in the case of grouped wafer data, the one or more processors 102 of the control system 101 may generate one or more histograms 132 for given data fields. The histograms 132 may be updated dynamically in the event a data grouping is altered. A pop-out window 135 displayed on display 104 may provide the details of the displayed histogram 132. The histogram details may include, but are not limited to, minimum "min," maximum "max," standard deviation "std dev," and the like.

In another aspect of the present invention, as shown in FIGS. 1B and 1D, one or more processors 102 of control system 101 may display one or more images 122 of one or more detected defects of a wafer 105 in the image display area 124 of the display device 104. In a further embodiment, in response to a signal from the user interface device indicative of a selection of a wafer for defect image display, one or more processors 102 of control system 101 may display one or more images 122 of one or more detected defects of a wafer 105 in the image display area 124 of the display device 104. For example, as shown in FIG. 1B, a user 112 may select a given wafer row 127 causing the one or more processors 102 to display one or more images 122 for the given wafer in an image display area 124. In a further embodiment, the one or more processors 102 of control system 101 may display one or more zoomed-in images 122 of one or more detected defects of the wafer in the image display area 124 of the display device 104.

Figure 1F:
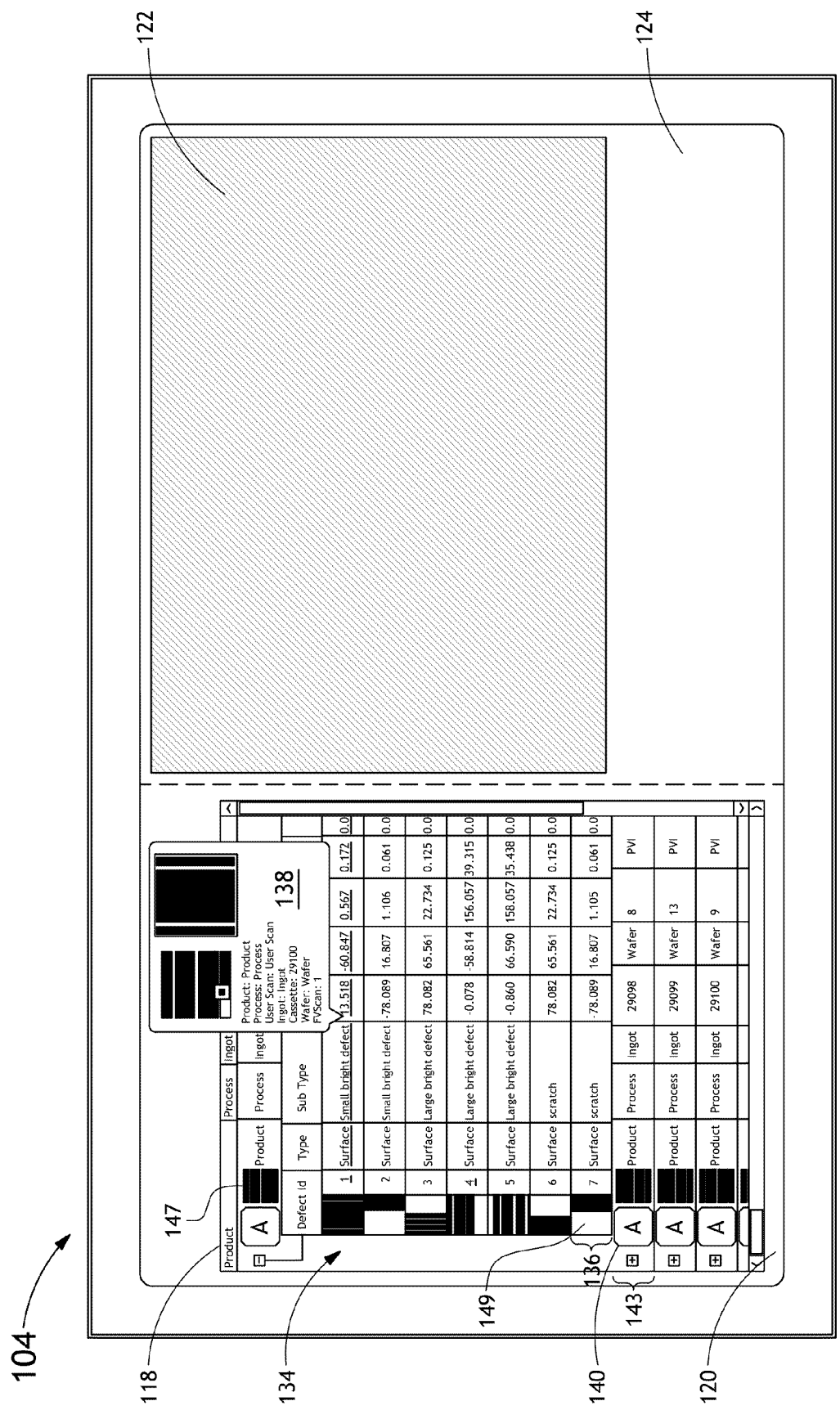
FIG. 1F is a schematic diagram of a display including a gallery display area and an image display area, in accordance with one embodiment of the present invention.

In another aspect of the present invention, as shown in FIGS. 1E and 1F, one or more processors 102 of control system 101 may display one or more images 122 of one or more detected defects of a wafer 105 in a pop-out window displayed in the gallery area 118 of the display device 104. In a further embodiment, in response to a signal from the user interface device 110 indicative of a selection of a wafer for defect image pop-up display, one or more processors 102 of control system 101 may display one or more images 122 of one or more detected defects of a wafer 105 in a pop-out window displayed in the gallery area 118 of the display device 104. For example, a user 112 may hover a cursor of the display device 104 over a given wafer row 133 (as shown in FIG. 1E) or a given defect row 136 causing the one or more processors 102 to launch a pop-up window (i.e., "tooltip") including one or more images of one or more of the defects detected on the wafer of the selected row 133. For instance, the one or more processors 102 may display a zoomed-out view 137 of the entire wafer associated with wafer row 133. Further, a zoomed-in view 139 of a selected defect (e.g., defect 1 of the wafer associated with wafer row 133) may be displayed by the one or more processors 102. In this regard, the area of the selected defect may be highlighted using a highlight region 141 on the zoomed-out view 137 of the wafer. In this regard, once the hierarchical tree view 118 of data is displayed the user 112 may navigate up and down the various levels of wafer data, selecting specific subgroups of wafers 105 or individual wafers in order to perform analysis. Each level can be expanded or collapsed, all the way to the individual defect level 139, providing the ability to display a thumbnail 137 for each wafer 105 indicating its overall grade. For both tree view forms as illustrated in FIG. 1E and FIG. 1F defect image pop-outs (i.e., tooltips) may be implemented.

In another aspect of the present invention, the one or more processors 102 of the control system 101 may display one or more images 122 of one or more detected defects of a wafer 105 in a static thumbnail positioned proximately to the pertinent data set. For example, as shown in FIG. 1F, an overall wafer view 147 may be display proximate to a wafer row 143, while a zoomed-in defect level image 149 may be displayed proximate to the defect level row 136. In this manner, the one or more processors 102 may display a zoomed-in defect level view 149 for each of the defects detected for a given wafer 105, whereby the selection of the wafer row 143 corresponding to a given wafer 105 acts to auto-spawn both the defect textual data in the data rows 136 as well as the static thumbnails 149 of each defect.

In another aspect of the present invention, the one or more processors 102 of the control system 101 may provide a visual indication for visually identifying at least one of a set of wafer data or a set of wafer group data as being within a selected tolerance range. Alternatively, the one or more processors 102 of the control system 101 may provide a visual indication for visually identifying at least one of a set of wafer data or a set of wafer group data as being outside a selected tolerance range. For example, as shown in FIG. 1F, an icon 140 may be displayed to indicate whether the selected set of wafer data 143 is within or outside of an acceptable tolerance range. For instance, the icon 140 may be textually (e.g., Yes/No, A/B, Good/Bad, and the like), symbolically (e.g., +/− and the like), or color (e.g., Green/Red, Blue/Red, and the like) coded to easily indicate to a user whether the data 143 adheres to the selected tolerance level.

The display device 104 may include any display device known in the art. In one embodiment, the display device 104 may include, but is not limited to, a liquid crystal display (LCD). In another embodiment, the display device 104 may include, but is not limited to, an organic light-emitting diode (OLED) based display. In another embodiment, the display device 104 may include, but is not limited to a CRT display. Those skilled in the art should recognize that a variety of display devices may be suitable for implementation in the present invention and the particular choice of display device may depend on a variety of factors, including, but not limited to, form factor, cost, and the like. In a general sense, any display device capable of integration with a user interface device (e.g., touchscreen, bezel mounted interface, keyboard, mouse, trackpad, and the like) is suitable for implementation in the present invention.

The user interface device 110 may include any user interface known in the art. For example, the user interface 106 may include, but is not limited to, a keyboard, a keypad, a touchscreen, a lever, a knob, a scroll wheel, a track ball, a switch, a dial, a sliding bar, a scroll bar, a slide, a handle, a touch pad, a paddle, a steering wheel, a joystick, a bezel input device or the like. In the case of a touchscreen interface device, those skilled in the art should recognize that a large number of touchscreen interface devices may be suitable for implementation in the present invention. For instance, the display device 104 may be integrated with a touchscreen interface, such as, but not limited to, a capacitive touchscreen, a resistive touchscreen, a surface acoustic based touchscreen, an infrared based touchscreen, or the like. In a general sense, any touchscreen interface capable of integration with the display portion of the display device 104 is suitable for implementation in the present invention. In another embodiment, the user interface 110 may include, but is not limited to, a bezel mounted interface. In the case of a bezel input device, the display device 104 may include a bezel equipped with one or more bezel mounted interface devices. For instance, the bezel mounted interface may include, but is not limited to, a hard key (or hard "button") disposed on the bezel of the display device 104. In a general sense, any bezel mounted interface capable of integration with the display device 104 is suitable for implementation in the present invention.

In another aspect, the one or more processors 102 are in communication with a memory medium 114. The memory medium 114 may be configured to store one or more sets of wafer inspection data in a wafer inspection database 116. In this regard, the one or more processors 102 of the controller 101 may store all or a portion of the wafer inspection data received by the one or more processors 102 (e.g., received from the inspection devices 106, received from an additional system or tool, received from a portable memory medium, such as a solid state memory device, a optical memory device, a magnetic memory device, and the like) in the wafer inspection database 116 maintained in memory 114. In addition, the one or more memory media 114 may store the program instructions suitable for execution by the communicatively coupled one or more processors 102. Program instructions 117 implementing methods such as those described herein may be transmitted over or stored on a carrier medium. The carrier medium may be a transmission medium such as a wire, cable, or wireless transmission link. The carrier medium may also include a memory medium 116 such as a read-only memory, a random access memory, a magnetic or optical disk, or a magnetic tape.

In general, the term "processor" may be broadly defined to encompass any device having one or more processors, which execute instructions from a memory medium. In this sense, the one or more processors 102 may include any microprocessor-type device configured to execute software algorithms and/or instructions. In one embodiment, the one or more processors 102 may consist of a desktop computer or other computer system (e.g., networked computer) configured to execute a program configured to operate the system 100, as described throughout the present disclosure. It should be recognized that the steps described throughout the present disclosure may be carried out by a single computer system or, alternatively, multiple computer systems. Moreover, different subsystems of the system 100, such as the display device 104 or the user interface device 110, may include a processor or logic elements suitable for carrying out at least a portion of the steps described above. Therefore, the above description should not be interpreted as a limitation on the present invention but merely an illustration.

Figure 2:
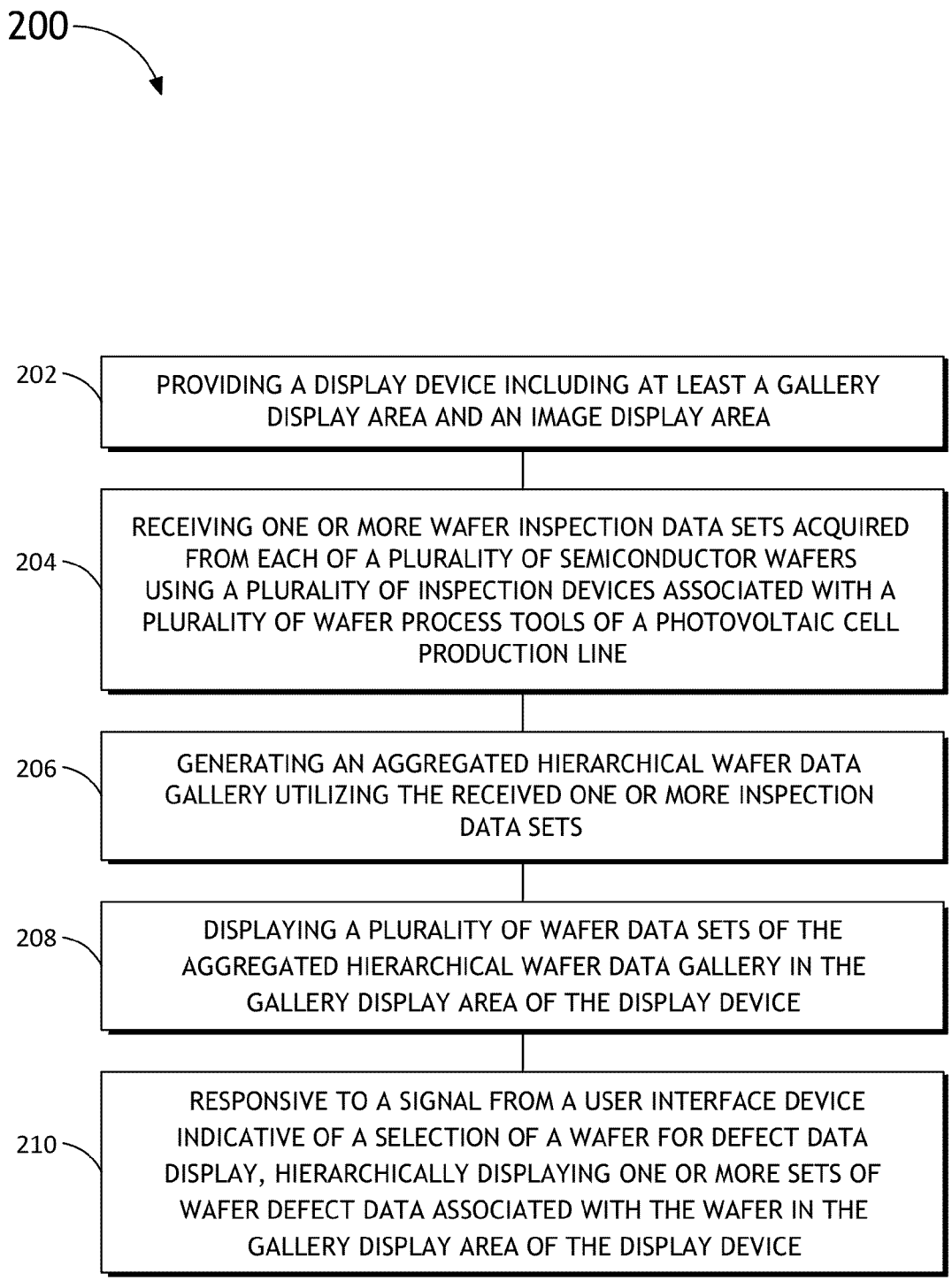
FIG. 2 is a flow chart illustrating a method for providing visualization of semiconductor wafer inspection data acquired in a photovoltaic cell production process, in accordance with one embodiment of the present invention.

FIG. 2 illustrates a method 200 for providing visualization of semiconductor wafer inspection data acquired during in a photovoltaic cell production process, in accordance with one embodiment of the present invention.

In step 202, a display device responsive to one or more user interface devices is provided. The display device may include any suitable display device known in the art, such as, but not limited to, a LCD or an OLED display. In step 204, one or more inspection data sets acquired from each of a plurality of semiconductor wafers 105 using a plurality of inspection devices 108 associated with a plurality of wafer process tools 106 of a photovoltaic cell production line may be received. For example, one or more processors 102 of a control system 101 may receive one or more inspection data sets acquired from each of a plurality of semiconductor wafers using a plurality of inspection devices associated with a plurality of wafer process tools of a photovoltaic cell production line. In step 206, an aggregated hierarchical wafer data gallery 118 may be generated utilizing the received one or more inspection data sets. For example, the one or more processors 102 of controller 101 may generate an aggregated hierarchical wafer data gallery utilizing the received one or more inspection data sets. In step 208, a plurality of wafer data sets of the aggregated hierarchical wafer data gallery may be displayed in the gallery display area 120 of the display device 104. For example, the one or more processors 102 of the control system 101 may display a plurality of wafer data sets of the aggregated hierarchical wafer data gallery 118 in the gallery display area 120 of the display device 104. In step 210, in response to a signal from the user interface device indicative of a selection of a wafer for defect data display, one or more sets of wafer defect data associated with the wafer may be hierarchically displayed in the gallery display area of the display device. For example, the one or more processors 102 of the control system 101 may hierarchically display one or more sets of wafer defect data associated with the wafer in the gallery display area 118 of the display device 104.

Figure 3:
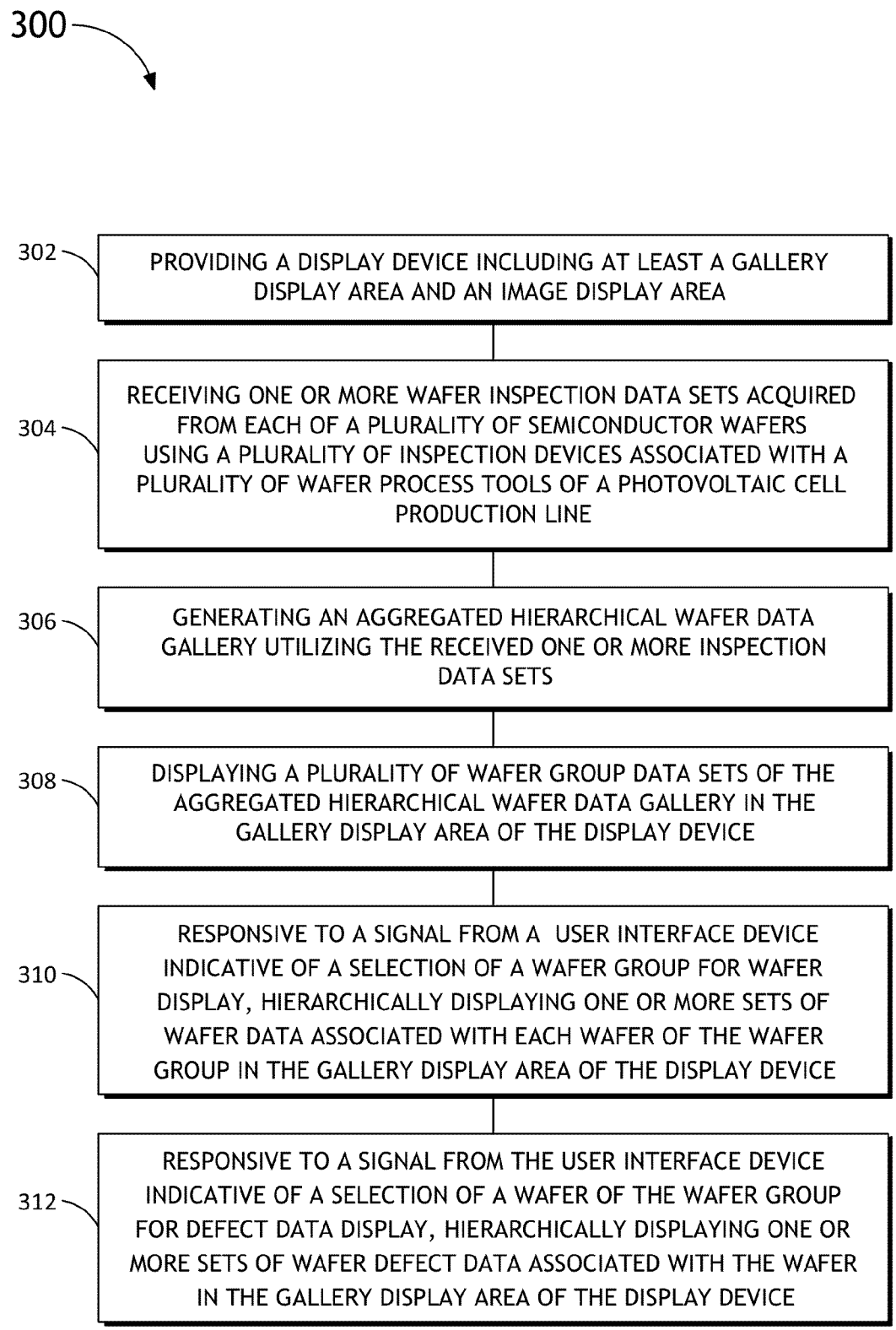
FIG. 3 is a flow chart illustrating a method for providing visualization of semiconductor wafer inspection data acquired in a photovoltaic cell production process, in accordance with one embodiment of the present invention.

FIG. 3 illustrates a method 300 for providing visualization of semiconductor wafer inspection data acquired during in a photovoltaic cell production process, in accordance with one embodiment of the present invention.

In step 302, a display device responsive to one or more user interface devices is provided. The display device may include any suitable display device known in the art, such as, but not limited to, a LCD or an OLED display. In step 304, one or more inspection data sets acquired from each of a plurality of semiconductor wafers 105 using a plurality of inspection devices 108 associated with a plurality of wafer process tools 106 of a photovoltaic cell production line may be received. For example, one or more processors 102 of a control system 101 may receive one or more inspection data sets acquired from each of a plurality of semiconductor wafers using a plurality of inspection devices associated with a plurality of wafer process tools of a photovoltaic cell production line. In step 306, an aggregated hierarchical wafer data gallery 118 may be generated utilizing the received one or more inspection data sets. For example, the one or more processors 102 of controller 101 may generate an aggregated hierarchical wafer data gallery utilizing the received one or more inspection data sets. In step 308, a plurality of wafer group data sets of the aggregated hierarchical wafer data gallery may be displayed in the gallery display area 120 of the display device 104. For example, the one or more processors 102 of the control system 101 may display a plurality of wafer group data sets of the aggregated hierarchical wafer data gallery 118 in the gallery display area 120 of the display device 104. In step 310, in response to a signal from the user interface device indicative of a selection of a wafer group for wafer display, one or more sets of wafer data associated with each wafer of the wafer group may be hierarchically displayed in the gallery display area 118 of the display device 104. For example, the one or more processors 102 of the control system 101 may hierarchically display one or more sets of wafer data associated with each wafer of the wafer group in the gallery display area 118 of the display device 104. In step 312, in response to a signal from the user interface device indicative of a selection of a wafer of the wafer group for defect data display, one or more sets of wafer defect data associated with the wafer may be hierarchically displayed in the gallery display area of the display device. For example, the one or more processors 102 of the control system 101 may hierarchically display one or more sets of wafer defect data associated with the wafer of the wafer group in the gallery display area 118 of the display device 104.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed:

1. A system for providing visualization of semiconductor wafer inspection data acquired in a photovoltaic cell production process, comprising:
   a display device, wherein the display device includes at least a data gallery display area and an imagery display area;
   a user interface device;
   a computer control system communicatively coupled to the display device and the user interface device, the computer control system configured for:
      receiving one or more inspection data sets acquired from each of a plurality of semiconductor wafers using a plurality of inspection devices associated with a plurality of wafer process tools of a photovoltaic cell production line;
      generating an aggregated hierarchical wafer data gallery utilizing the received one or more inspection data sets, wherein said generating the aggregated hierarchical wafer data gallery includes defining a plurality of data grouping levels of the received one or more inspection data sets; and
      displaying at least a portion of the aggregated hierarchical wafer data gallery in the gallery display area of the display device.

2. The system of claim 1, wherein the displaying the aggregated hierarchical wafer data gallery in the gallery display area of the display device comprises:
   displaying a plurality of wafer data sets of the aggregated hierarchical wafer data gallery in the gallery display area of the display device; and
   responsive to a signal from the user interface device indicative of a selection of a wafer for defect data display, hierarchically displaying one or more sets of wafer defect data associated with the wafer in the gallery display area of the display device.

3. The system of claim 1, wherein the displaying the aggregated hierarchical wafer data gallery in the gallery display area of the display device comprises:
   displaying a plurality of wafer group data sets of the aggregated hierarchical wafer data gallery in the gallery display area of the display device;
   responsive to a signal from the user interface device indicative of a selection of a wafer group for wafer display, hierarchically displaying one or more sets of wafer data associated with each wafer of the wafer group in the gallery display area of the display device; and
   responsive to a signal from the user interface device indicative of a selection of a wafer of the wafer group for defect data display, hierarchically displaying one or more sets of wafer defect data associated with the wafer in the gallery display area of the display device.

4. The system of claim 1, wherein the displaying the aggregated hierarchical wafer data gallery in the gallery display area of the display device comprises:
   displaying a selected set of statistical characteristics associated with a selected portion of the received one or more inspection data sets acquired from each of a plurality of semiconductor wafers.

5. The system of claim 4, wherein the displaying a selected set of statistical characteristics associated with a selected portion of the received one or more inspection data sets acquired from each of a plurality of semiconductor wafers comprises:
   displaying a set of generated summary statistical characteristics associated with a selected portion of the received one or more inspection data sets acquired from each of a plurality of semiconductor wafers.

6. The system of claim 4, wherein the displaying a selected set of statistical characteristics associated with a selected portion of the received one or more inspection data sets acquired from each of a plurality of semiconductor wafers comprises:
   displaying one or more statistical distribution charts associated with a selected wafer group data set.

7. The system of claim 6, wherein the displaying one or more statistical distribution charts associated with a selected wafer group data sets comprises:
   responsive to a signal from the user interface device indicative of a selection of a selected wafer group data set, displaying one or more statistical distribution charts associated with a selected wafer group data set.

8. The system of claim 1, wherein the computer control system is further configured to:
   responsive to a signal from the user interface device indicative of a selection of a wafer for defect image display, displaying one or more images of one or more detected defects of the wafer in the image display area of the display device.

9. The system of claim 8, wherein the computer control system is further configured to:
   responsive to a signal from the user interface device indicative of a selection of a wafer for defect image display, displaying one or more zoomed-in images of one or more detected defects of the wafer in the image display area of the display device.

10. The system of claim 1, wherein the computer control system is further configured to:
    responsive to a signal from the user interface device indicative of a selection of a wafer for defect image pop-up display, displaying one or more thumbnail images of one or more detected defects of the wafer in a pop-up region of the gallery display area of the display device.

11. The system of claim 10, wherein the computer control system is further configured to:
    responsive to a signal from the user interface device indicative of a selection of a wafer for defect image pop-up display, displaying one or more zoomed-in thumbnail images of one or more detected defects of the wafer in a pop-up region of the gallery display area of the display device.

12. The system of claim 1, wherein the hierarchical displayed one or more sets of wafer defect data associated with the wafer comprises:
    defect data associated with each detected defect of the wafer.

13. The system of claim 12, wherein the defect data associated with each detected defect of the wafer comprises:
    position data associated with each detected defect of the wafer.

14. The system of claim 12, wherein the defect data associated with each detected defect of the wafer comprises:
    size data associated with each detected defect of the wafer.

15. The system of claim 1, wherein the displaying the aggregated hierarchical wafer data gallery in the gallery display area of the display device comprises:

visually identifying at least one of a set of wafer data or a set of wafer group data as being within a selected tolerance range.

16. The system of claim 1, wherein the displaying the aggregated hierarchical wafer data gallery in the gallery display area of the display device comprises:

visually identifying at least one of a set of wafer data or a set of wafer group data as being outside a selected tolerance range.

17. The system of claim 1, wherein the computer control system is further configured to:

visually identify one or more defects of the received one or more inspection data sets having a parameter outside a selected tolerance range.

18. The system of claim 1, wherein the computer control system comprises:

one or more processors; and
a non-transitory computer-readable storage medium containing instructions executable by the one or more processors.

19. The system of claim 1, wherein the display device comprises at least one of a liquid crystal display (LCD) device, an organic light emitting diode (OLED) display device, a light emitting diode (LED) display device, a plasma display device, or a cathode rate tube (CRT) display device.

20. The system of claim 1, wherein the user interface device comprises at least one of a keyboard, a keypad, a touchpad, a trackball, a mouse, a touchscreen device, an input device disposed on a bezel of the display device or a joystick.

21. A method for providing visualization of semiconductor wafer inspection data acquired in a photovoltaic cell production process, comprising:

providing a display device including at least a gallery display area and an image display area, the display device being responsive to one or more user interface devices;

receiving one or more inspection data sets acquired from each of a plurality of semiconductor wafers using a plurality of inspection devices associated with a plurality of wafer process tools of a photovoltaic cell production line;

generating an aggregated hierarchical wafer data gallery utilizing the received one or more inspection data sets, wherein said generating the aggregated hierarchical wafer data gallery includes defining a plurality of data grouping levels of the received one or more inspection data sets;

displaying a plurality of wafer data sets of the aggregated hierarchical wafer data gallery in the gallery display area of the display device; and responsive to a signal from the user interface device indicative of a selection of a wafer for defect data display, hierarchically displaying one or more sets of wafer defect data associated with the wafer in the gallery display area of the display device.

22. A method for providing visualization of semiconductor wafer inspection data acquired in a photovoltaic cell production process, comprising:

providing a display device including at least a gallery display area and an image display area, the display device being responsive to one or more user interface devices;

one or more inspection data sets acquired from each of a plurality of semiconductor wafers using a plurality of inspection devices associated with a plurality of wafer process tools of a photovoltaic cell production line;

generating an aggregated hierarchical wafer data gallery utilizing the received one or more inspection data sets, wherein said generating the aggregated hierarchical wafer data gallery includes defining a plurality of data grouping levels of the received one or more inspection data sets;

displaying a plurality of wafer group data sets of the aggregated hierarchical wafer data gallery in the gallery display area of the display device;

responsive to a signal from the user interface device indicative of a selection of a wafer group for wafer display, hierarchically displaying one or more sets of wafer data associated with each wafer of the wafer group in the gallery display area of the display device; and responsive to a signal from the user interface device indicative of a selection of a wafer of the wafer group for defect data display, hierarchically displaying one or more sets of wafer defect data associated with the wafer in the gallery display area of the display device.

\* \* \* \* \*